United States Patent
Kim et al.

(10) Patent No.: US 10,143,770 B2
(45) Date of Patent: Dec. 4, 2018

(54) PHOTOCATALYTIC APPARATUS AND HVAC EQUIPMENT FOR VEHICLE COMPRISING SAME

(71) Applicant: Hanon Systems, Daejeon (KR)

(72) Inventors: Jae Ho Kim, Daejeon (KR); Ki Hong Kim, Daejeon (KR); Ji-Yong Park, Daejeon (KR); Tae Yong Park, Daejeon (KR); Yong Jun Jee, Daejeon (KR)

(73) Assignee: HANON SYSTEMS, Daejeon (KR)

( * ) Notice: Subject to any disclaimer, the term of this patent is extended or adjusted under 35 U.S.C. 154(b) by 0 days.

(21) Appl. No.: 15/541,670

(22) PCT Filed: Mar. 22, 2016

(86) PCT No.: PCT/KR2016/002853
§ 371 (c)(1),
(2) Date: Jul. 5, 2017

(87) PCT Pub. No.: WO2016/195221
PCT Pub. Date: Dec. 8, 2016

(65) Prior Publication Data
US 2018/0264162 A1     Sep. 20, 2018

(30) Foreign Application Priority Data
Jun. 5, 2015   (KR) .................. 10-2015-0079930

(51) Int. Cl.
*A61L 9/20*      (2006.01)
*B01J 21/00*     (2006.01)
(Continued)

(52) U.S. Cl.
CPC ............... *A61L 9/205* (2013.01); *B01J 21/04* (2013.01); *B01J 21/063* (2013.01); *B01J 35/004* (2013.01);
(Continued)

(58) Field of Classification Search
CPC .. A61L 9/205; A61L 2209/12; A61L 2209/15; A61L 2209/16; B01J 21/04;
(Continued)

(56) References Cited

U.S. PATENT DOCUMENTS

| | | | |
|---|---|---|---|
| 2011/0034908 A1* | 2/2011 | Hyde | A61M 5/14276 604/891.1 |
| 2014/0158641 A1* | 6/2014 | Mukherjee | C02F 1/32 210/764 |

(Continued)

FOREIGN PATENT DOCUMENTS

| | | |
|---|---|---|
| JP | 2549032 Y | 5/1997 |
| JP | 2006050988 A | 2/2006 |

(Continued)

*Primary Examiner* — Nicole Ippolito
(74) *Attorney, Agent, or Firm* — Norton Rose Fulbright US LLP (57) ABSTRACT

The present invention relates to a photocatalytic apparatus and a heating, ventilating, and air conditioning (HVAC) equipment for a vehicle comprising the same and, more specifically, to a photocatalytic apparatus and HVAC equipment for a vehicle comprising the same, wherein the photocatalytic apparatus may sterilize and deodorize an evaporator in addition to purifying air introduced into an HVAC case and may continuously maintain sterilization and deodorization functions by efficiently radiating heat generated from the photocatalytic apparatus.

15 Claims, 11 Drawing Sheets

(51) Int. Cl.
 *B01J 21/06* (2006.01)
 *B01J 21/04* (2006.01)
 *B01J 35/00* (2006.01)
 *B01J 35/10* (2006.01)
 *B60H 3/00* (2006.01)

(52) U.S. Cl.
 CPC ....... *B01J 35/0013* (2013.01); *B01J 35/1019* (2013.01); *B60H 3/0078* (2013.01); *A61L 2209/12* (2013.01); *A61L 2209/15* (2013.01); *A61L 2209/16* (2013.01)

(58) Field of Classification Search
 CPC .... B01J 21/063; B01J 21/0013; B01J 21/004; B60H 3/0078
 USPC ... 250/453.11, 454.11, 455.11, 493.1, 494.1, 250/504 R
 See application file for complete search history.

(56) References Cited

U.S. PATENT DOCUMENTS

| | | | |
|---|---|---|---|
| 2015/0114912 A1* | 4/2015 | Taghipour | C02F 1/325 210/748.11 |
| 2017/0313611 A1* | 11/2017 | Huynh | C02F 9/005 |
| 2018/0019476 A1* | 1/2018 | Qiao | H01M 2/347 |

FOREIGN PATENT DOCUMENTS

| KR | 100945599 B1 | 3/2010 |
|---|---|---|
| KR | 101346603 B1 | 1/2014 |
| KR | 101431562 B1 | 8/2014 |
| KR | 101442155 B1 | 9/2014 |
| KR | 20150024011 A | 3/2015 |
| KR | 20150025967 A | 3/2015 |

\* cited by examiner

PHOTOCATALYTIC APPARATUS AND HVAC EQUIPMENT FOR VEHICLE COMPRISING SAME

This application is a 371 of International Application No. PCT/KR2016/002853 filed Mar. 22, 2016, which claims priority from Korean Patent Application No. 10-2015-0079930 filed Jun. 5, 2015, each of which is incorporated herein by reference in its entirety for all purposes.

TECHNICAL FIELD

The present invention relates to a photocatalytic apparatus and a heating, ventilating, and air conditioning (HVAC) equipment for a vehicle comprising the same and, more specifically, to a photocatalytic apparatus and HVAC equipment for a vehicle comprising the same, in which the photocatalytic apparatus may sterilize and deodorize an evaporator in addition to purifying air introduced into an HVAC case and may continuously maintain sterilization and deodorization functions by efficiently radiating heat generated from the photocatalytic apparatus.

BACKGROUND ART

A heating, ventilating, and air conditioning (HVAC) equipment for a vehicle is an apparatus for heating or cooling air by introducing air outside the vehicle into the interior of the vehicle or circulating the air in the interior of the vehicle to cool or heat the interior of the vehicle and includes an evaporator for cooling an inside of an HVAC case, a heater core for a heating action, and a blowing mode switching door for selectively blowing the air cooled or heated by the evaporator or the heater core into each part of the interior of the vehicle.

Meanwhile, as a vehicle penetration rate is not only continuously increased but time in which a user stays in a vehicle is also increased, researches for maintaining comfort of the interior of the vehicle have been conducted, but as the interior of the vehicle is narrow and closed to be prone to be polluted and the pollution of the interior of the vehicle is becoming more and more heavy due to fine dust and various pollutants of a downtown area, an air purifier for a vehicle that purifies indoor air of a vehicle has recently been developed.

As an example, a cooling apparatus with a deodorizer for a vehicle has been disclosed in Japanese Patent Publication No. 2549032 (Registration date: May 30, 1997, entitled "Cooling apparatus with a deodorizer for a vehicle).

Figure 1:
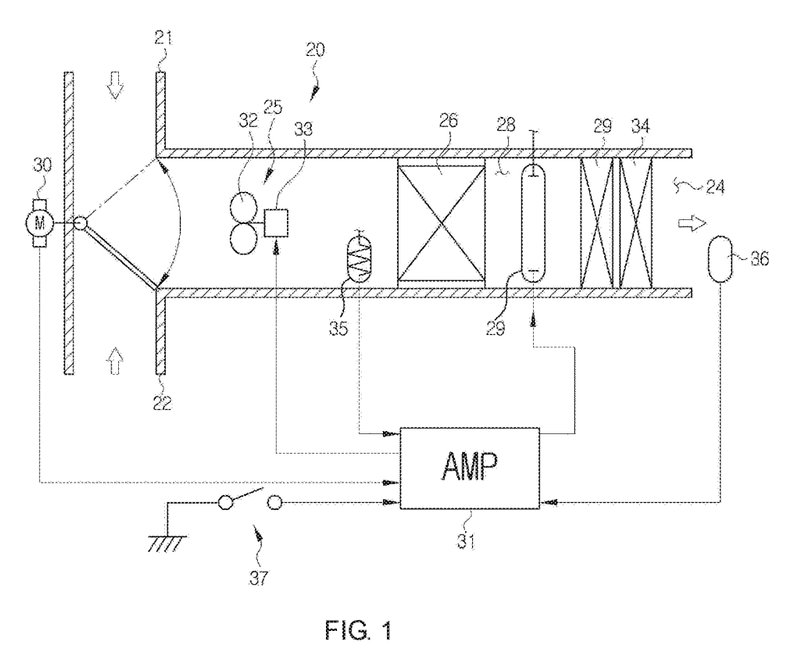
FIG. 1 is a cross-sectional view illustrating the existing cooling apparatus with a deodorizer for a vehicle.

FIG. 1 is a cross-sectional view illustrating the existing cooling apparatus with a deodorizer for a vehicle.

As illustrated in FIG. 1, the existing cooling apparatus with a deodorizer for a vehicle includes a case 20 having an outdoor air inlet 21 and an indoor air inlet 22 provided therein and an intake door 23 rotatably provided to selectively open and close the outdoor air inlet 21 and the indoor air inlet 22. An actuator 30 connected to a rotating shaft of the intake door 23 is controlled by a controller 31. A downstream side of the intake door 23 is provided with a blower 25 for blowing the air introduced from the indoor and outdoor air inlets 21 and 22 to the downstream side and the blower 25 includes a fan 32 and a motor 33 rotating the fan 32. An evaporator 26 is provided on the downstream side of the blower 25 and cools air by exchanging heat with the air passing therethrough. An air passage 28 on the downstream side of the evaporator 26 is provided with a photocatalytic filter 27 for generating active oxygen by irradiation of long wavelength light.

The photocatalytic filter 27 produces active oxygen by irradiation of an ultraviolet lamp 29. Here, the active oxygen oxidizes and decomposes substances giving out an odor to make the substances into an extremely low-concentration oxidizable compound. The ultraviolet lamp 29 is disposed between the evaporator 26 and the photocatalytic filter 27. A downstream side of the photocatalytic filter 27 is provided with a metal catalytic filter 34 for removing ozone contained in flowing air. Reference numerals 35, 36, 37, and 24 that are not explained each represent a temperature sensor, a sensor for sensing an odor level, a fan switch, and an air outlet.

However, the existing cooling apparatus with a deodorizer for a vehicle may not be applied to a vehicle due to various environmental factors because the ultraviolet lamp 29 used as a light source of the photocatalyst contains mercury harmful to a human body.

In addition, since the photocatalytic filter 27 is installed on the downstream side of the evaporator 26 to adsorb and deodorize the odor generated from the evaporator 26, there is a problem in that the photocatalytic filter needs to be replaced due to a decrease in an air volume when there is a large amount of dust.

In addition, the existing cooling apparatus with a deodorizer for a vehicle has a problem in that the ultraviolet lamp 29 and the photocatalytic filter 27 are separate components and therefore the assembling performance deteriorates.

DISCLOSURE

Technical Problem

An object of the present invention is to provide a photocatalytic apparatus and HVAC equipment for a vehicle comprising the same, in which the photocatalytic apparatus may sterilize and deodorize an evaporator in addition to purifying air introduced into an HVAC case and may continuously maintain sterilization and deodorization functions by efficiently radiating heat generated from the photocatalytic apparatus.

In particular, an object of the present invention is to provide a photocatalytic apparatus and HVAC equipment for a vehicle comprising the same, in which a catalytic part including a cylindrical carrier is formed and a distance between a light source and an end of a bottom surface of the carrier is constant to make an arrival distance of light irradiated from the light source constant, thereby considerably increasing sterilizing and deodorizing power.

Technical Solution

In one general aspect, a photocatalytic apparatus includes: a body; a light source part including an LED and a substrate to which the LED is fixed to irradiate ultraviolet (UV) light and fixed to the body; a catalytic part generating a photocatalytic reaction by light irradiated from the light source part while being fixed to the body to produce peroxygen radicals and including a cylindrical carrier and a coating layer fixed to the carrier in which a catalyst liquefied in a gel state by adding a co-catalyst and an acidic additive is carried; and a heat radiating part provided in the light source part to emit heat generated from the light source part.

The catalytic part may be fixed to the body so that a distance between the LED and an end of a bottom surface of the carrier is constant.

The body may include: a support part supporting the substrate; a space forming part extending from the support part and forming a gap between the LED and the catalytic part; and a catalyst receiving part extending from the space forming part to fix the catalytic part.

The space forming part may be inclined so that a width of the space forming part is widened in a light irradiating direction of the light source part from the support part.

The body may be provided with a drainage hole through which moisture is discharged.

The drainage hole may be formed at an inclined lower side of the space forming part in a state in which the photocatalytic apparatus is mounted.

A surface of the substrate opposite to the catalytic part may be coated with a moisture-proof material.

The substrate may be a heat radiating substrate.

The catalyst may include titanium oxide particulated at a size of 10 nm to 60 nm and a surface area value of the titanium oxide may be 330 $m^2/g$ or more.

The co-catalyst may be alumina.

In another general aspect, a heating, ventilating, and air conditioning (HVAC) equipment includes: an HVAC case forming a space to which introduced air is transferred and provided with a vent through which air is discharged; an evaporator provided inside the HVAC case; a heater core provided at a back side of the HVAC case in an air flow direction; and the photocatalytic apparatus as described above.

The photocatalytic apparatus may be provided at a front side of the evaporator in an air flow direction.

A predetermined area of the HVAC case may be hollow and thus a mounting hole closed by the body may be provided, and the body may be provided with a fixing part for being fixed to the HVAC case.

In the photocatalytic apparatus, the fixing part may protrude from a side where the space forming part and the support part are formed so that the catalytic part is positioned inside the HVAC case and the space forming part is positioned outside the HVAC case, with respect to an outer surface of the HVAC case.

The photocatalytic apparatus may be mounted on one side of the HVAC case.

Advantageous Effects

According to the photocatalytic apparatus and the HVAC equipment for a vehicle comprising the same of the exemplary embodiment of the present invention, it is possible to sterilize and deodorize the evaporator in addition to purifying the air introduced into the HVAC case, and continuously maintain the sterilization and deodorization functions by efficiently radiating the heat generated from the photocatalytic apparatus.

In particular, according to the photocatalytic apparatus and the HVAC equipment for a vehicle comprising the same of the exemplary embodiment of the present invention, the catalytic part including the cylindrical carrier may be formed and the distance between the light source and the end of the bottom surface of the carrier may be constant to make the arrival distance of light irradiated from the light source constant, thereby considerably increasing the sterilizing and deodorizing power.

BEST MODE

Hereinafter, a photocatalytic apparatus 100 according to an exemplary embodiment of the present invention having the above-mentioned characteristics will be described in more detail with reference to the accompanying drawings.

Figure 2:
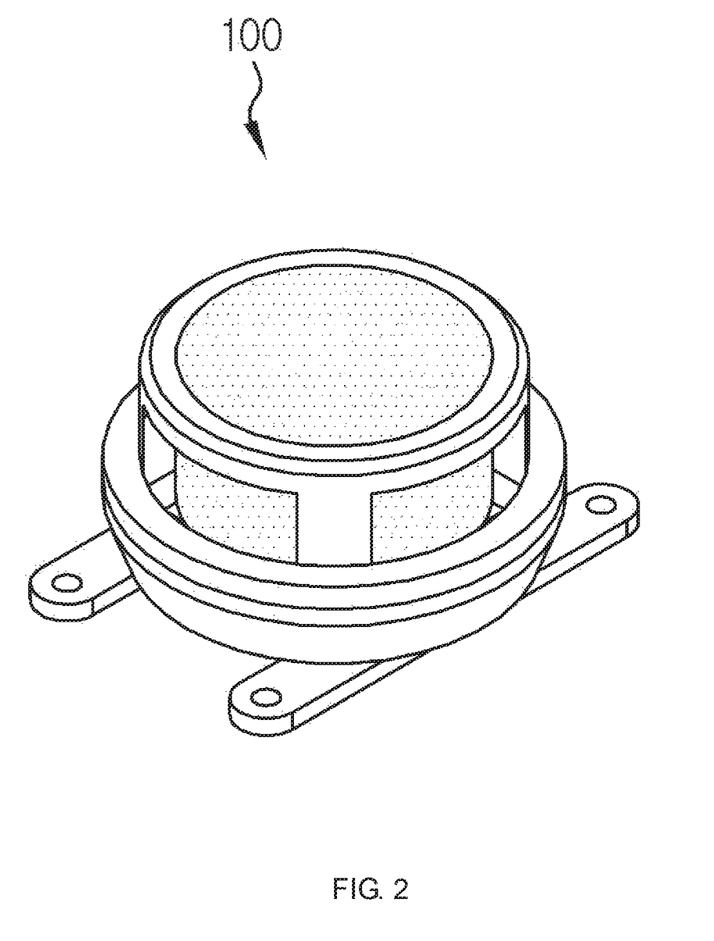
FIGS. 2 and 3 are perspective views illustrating a photocatalytic apparatus according to an exemplary embodiment of the present invention.
Figure 3:
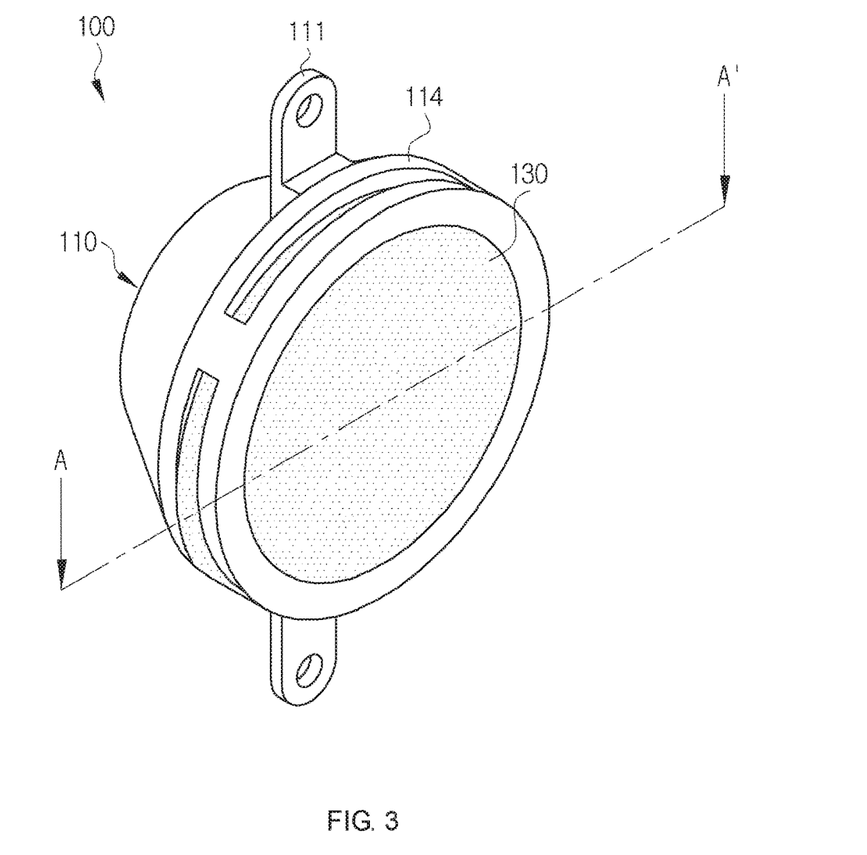
Figure 4:
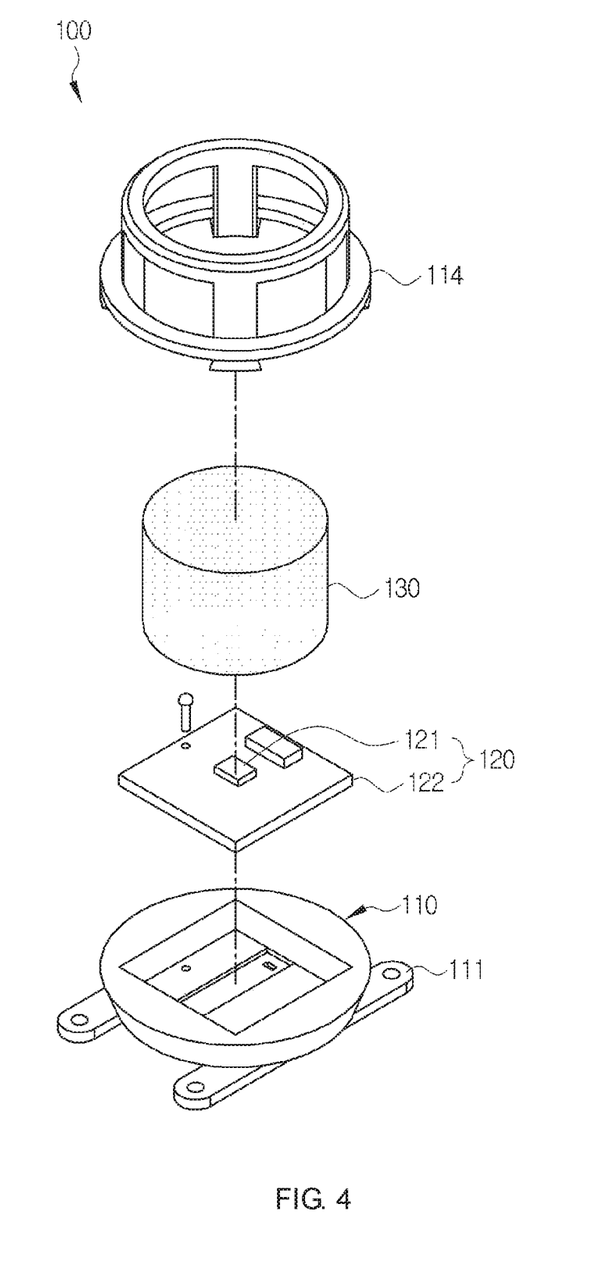
FIG. 4 is an exploded perspective view illustrating the photocatalytic apparatus according to the exemplary embodiment of the present invention.
Figure 5:
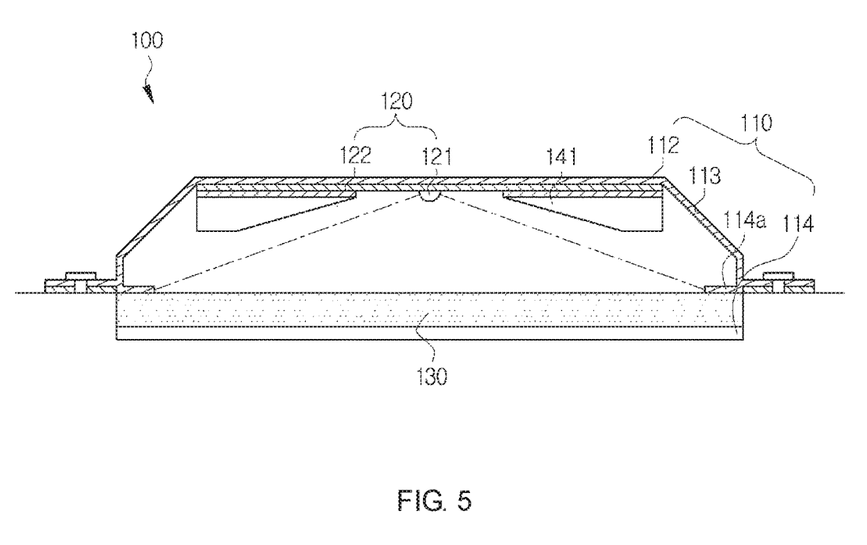
FIG. 5 is a cross-sectional view illustrating the photocatalytic apparatus according to the exemplary embodiment of the present invention.
Figure 6:
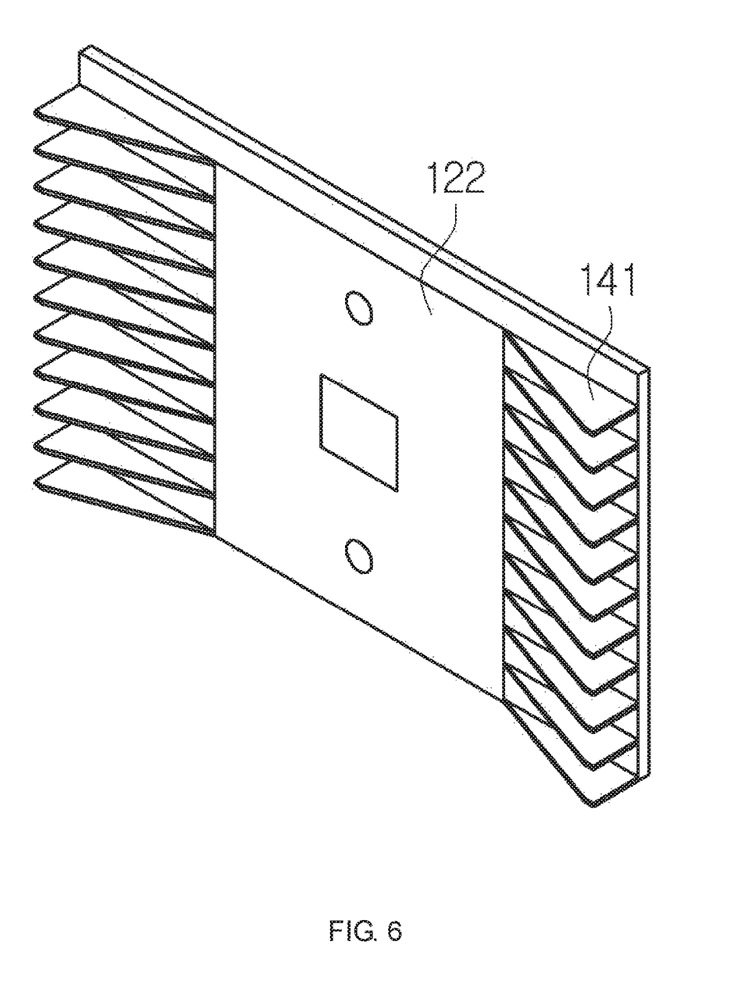
FIG. 6 is a view illustrating a first heat radiating fin provided in a photocatalytic apparatus according to the exemplary embodiment of the present invention.
Figure 7:
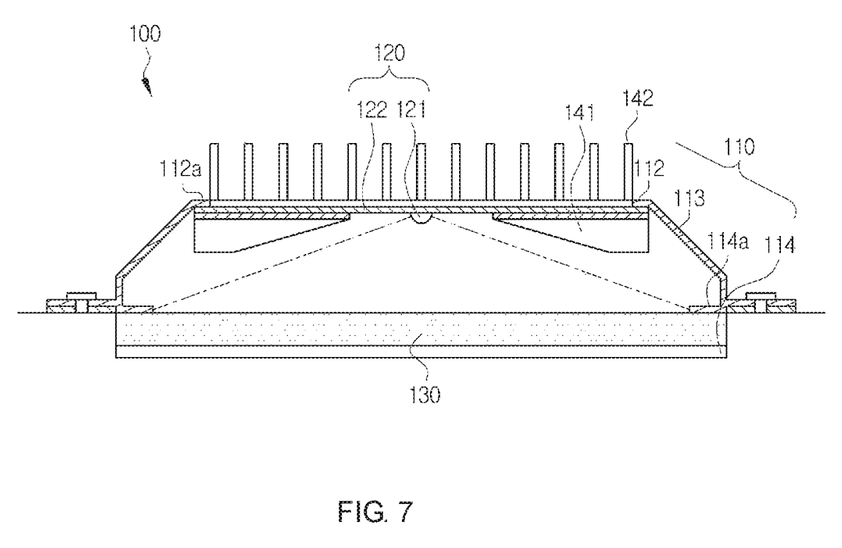
FIG. 7 is a view illustrating a second heat radiating fin provided in a photocatalytic apparatus according to the exemplary embodiment of the present invention.
Figure 8:
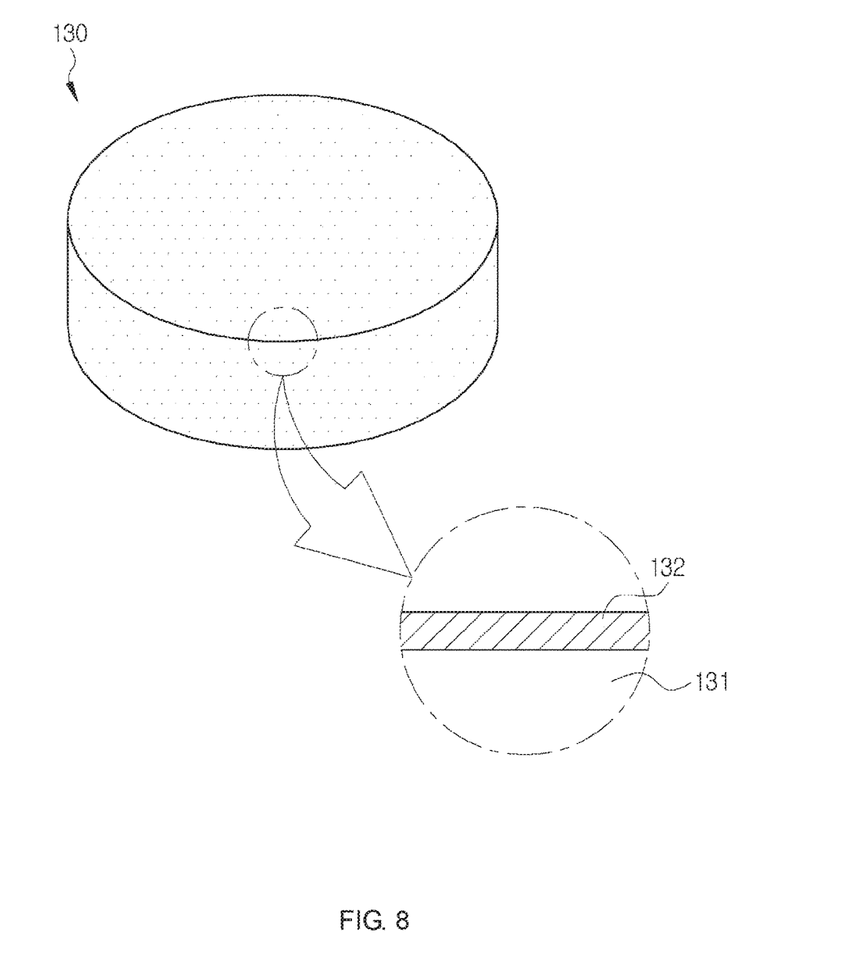
FIG. 8 is a view illustrating a catalytic part of the photocatalytic apparatus according to the exemplary embodiment of the present invention.
Figure 9:
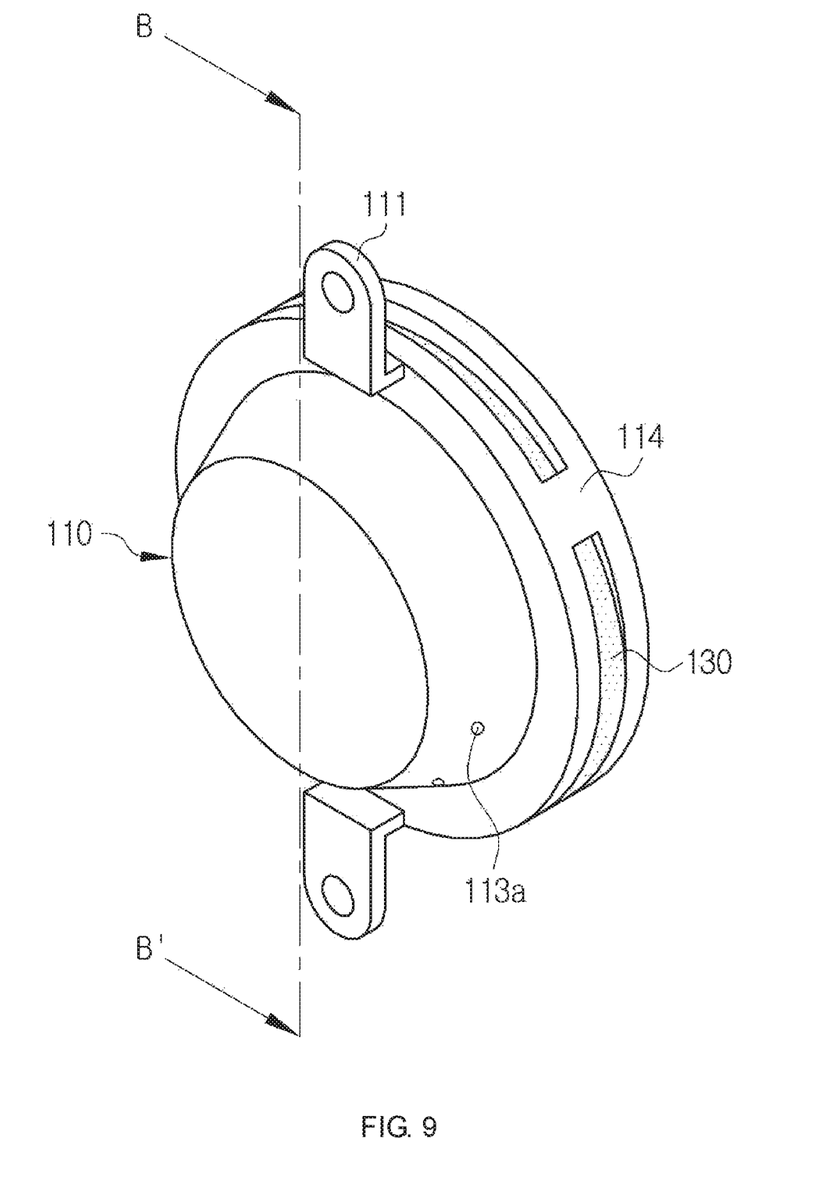
FIG. 9 is a perspective view illustrating the photocatalytic apparatus according to another exemplary embodiment of the present invention.
Figure 10:
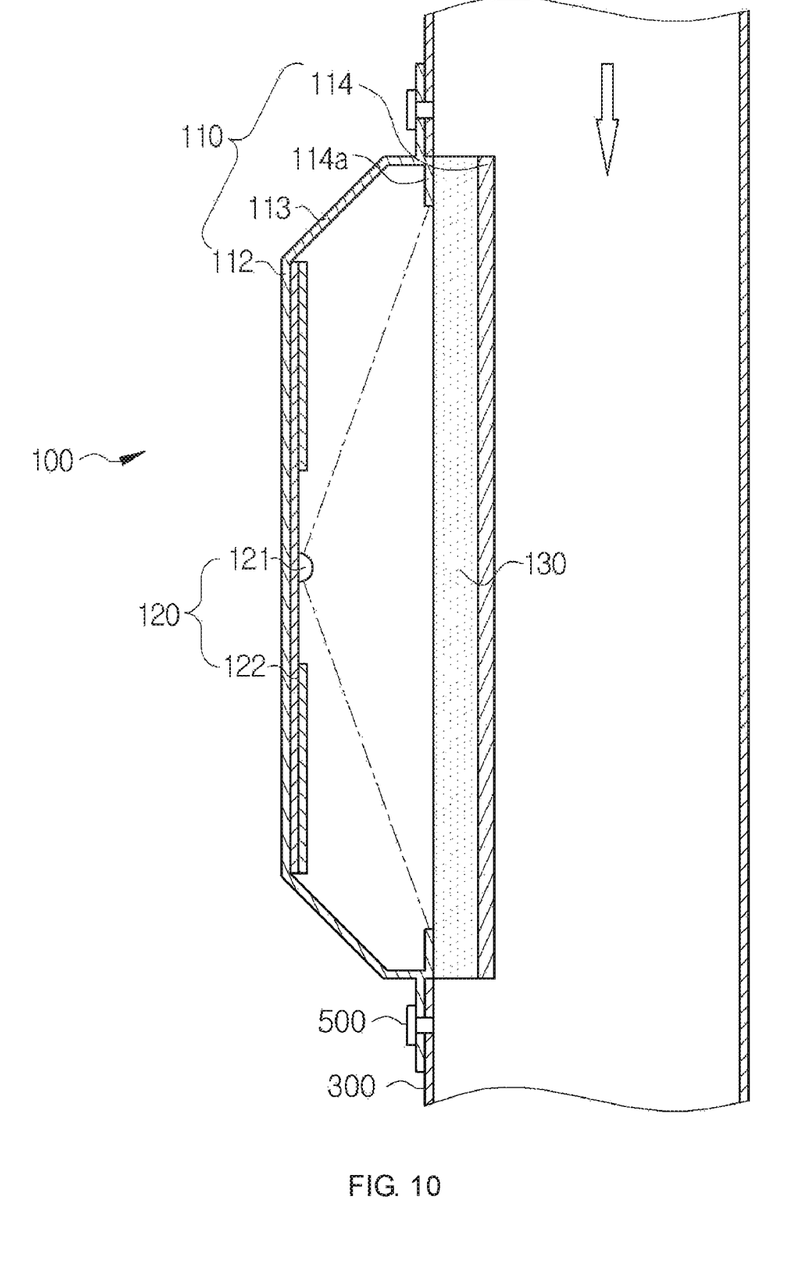
FIG. 10 is a cross-sectional view illustrating a shape in which the photocatalytic apparatus according to the exemplary embodiment of the present invention is mounted.
Figure 11:
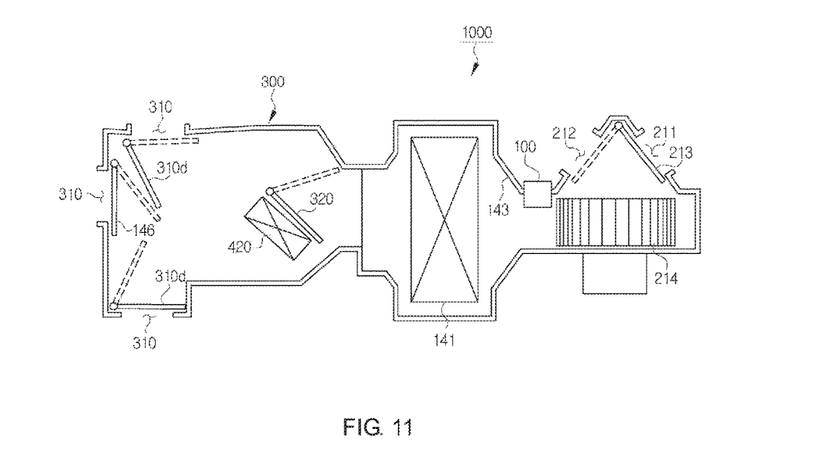
FIGS. 11 and 12 are a schematic view and a perspective view illustrating a heating, ventilating, and air conditioning (HVAC) equipment according to an exemplary embodiment of the present invention.
Figure 12:
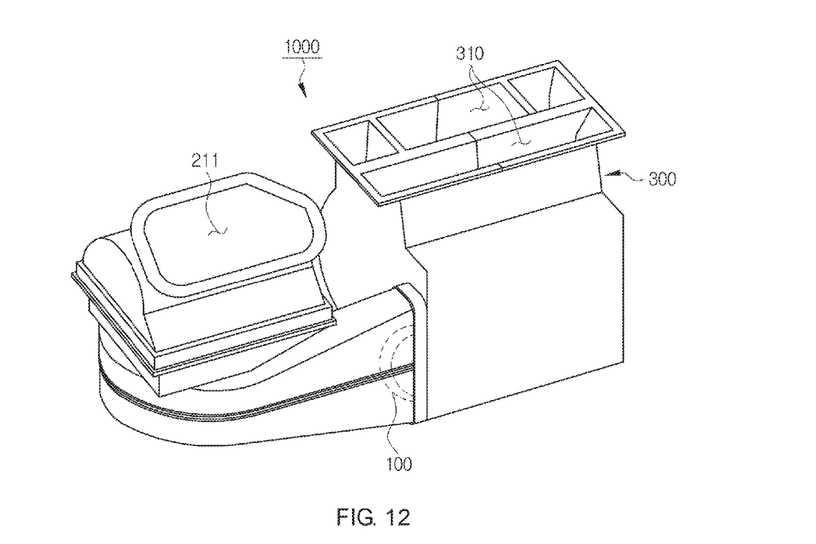

FIGS. 2 and 3 are perspective views illustrating a photocatalytic apparatus according to an exemplary embodiment of the present invention, FIG. 4 is an exploded perspective view illustrating the photocatalytic apparatus according to the exemplary embodiment of the present invention, FIG. 5 is a cross-sectional view illustrating the photocatalytic apparatus according to the exemplary embodiment of the present invention, FIG. 6 is a view illustrating a first heat radiating fin provided in a photocatalytic apparatus according to the exemplary embodiment of the present invention, FIG. 7 is a view illustrating a second heat radiating fin provided in a photocatalytic apparatus according to the exemplary embodiment of the present invention, FIG. 8 is a view illustrating a catalytic part of the photocatalytic apparatus according to the exemplary embodiment of the present invention, FIG. 9 is a perspective view illustrating the photocatalytic apparatus according to another exemplary embodiment of the present invention, FIG. is a cross-sectional view illustrating a shape in which the photocatalytic apparatus according to the exemplary embodiment of the present invention is mounted, and FIGS. 11 and 12 are a schematic view and a perspective view illustrating a heating, ventilating, and air conditioning (HVAC) equipment according to an exemplary embodiment of the present invention.

As illustrated in FIGS. 2 to 10, the photocatalytic apparatus 100 according to the exemplary embodiment of the present invention includes a body 110, a light source part 120, a catalytic part 130, and a heat radiating part.

The body 110 supports the light source part 120 and the catalytic part 130 and is provided with a fixing part 111 for fixing a heating, ventilating, and air conditioning (HVAC)

case 300 of an HVAC equipment 1000 for a vehicle, such that the body 110 is fixed to the HVAC case 300 of an HVAC equipment 1000 for a vehicle.

At this time, a shape of the fixing part 111 may be variously formed to be fixed to the HVAC case 300.

In addition, the body 110 includes a support part 112, a space forming part 113, and a catalyst receiving part 114.

The support part 112 is a part for supporting a substrate 122 of the light source part 120 and the space forming part 113 extends from the support part 112 toward the catalytic part 130 to form a gap between an LED 121 and the catalytic part 130 so that light irradiated from the LED 121 of the light source part 120 is transmitted to the catalytic part 130.

At this time, the space forming part 113 is inclined to have a width increased from the support part 112 toward a direction in which light of the light source part 120 is irradiated (direction in which the catalytic part 130 is formed) and guides the light irradiated from the light source part 120 mounted on the support part 112 to the catalytic part 130 so as to concentrate the light on the catalytic part 130, thereby increasing a reaction amount of a catalyst.

As a result, a generation quantity of peroxygen radicals is increased and thus the sterilization and deodorizing effect can be increased.

The catalyst receiving part 114 is a part where the catalytic part 130 is provided and may be formed to guide air in the HVAC case 300 of the HVAC equipment 1000 for a vehicle to the catalytic part 130.

In particular, one surface of the catalytic part 130 (opposite surface of a side where the support part 112 is provided) needs to be formed so as to be exposed to the inside of the HVAC case 300.

The catalyst receiving part 114 may be slidably coupled to the catalytic part 130 so that the catalytic part 130 may be detached, thereby facilitating the mounting and checking of the catalytic part 130. In addition thereto, the catalyst receiving part 114 may have more various forms in which the catalytic part 130 may be detached and attached.

The light source part 120 is a part irradiating ultraviolet light while being fixed to the body 110 and includes a light emitting diode (LED) 121 and a substrate 122 to which the LED 121 is fixed.

The LED 121 which irradiates ultra violet-A (UVA) light or ultra violet-C (UVC) light having a wavelength of 400 nm or less may solve the problem with mercury which has been a problem of the existing mercury lamp and effectively irradiate light with small power.

At this time, the UVA is relatively cheaper and therefore may be advantageous in cost and may effectively activate a photocatalytic reaction of a photocatalytic carrier and the UVC is relatively expensive but acts to activate the photocatalytic reaction and at the same time may perform the sterilization function to improve the sterilization efficiency.

The light source part 120 may be provided in two or more corresponding to the size of the catalytic part 130. In the present invention, the meaning that at least two light source parts 120 are provided is defined as including both cases where the LED 121 and the substrate 122 therefor are each provided in two or more and at least two LEDs 121 are provided on one substrate 122.

Needless to say, when at least two LEDs 121 are provided, the LEDs 121 that irradiate the UVA light and the UVC light may be provided.

The catalytic part 130 generates the photocatalytic reaction by the light irradiated from the light source part 120 to produce the peroxygen radicals.

The catalytic part 130 generates the photocatalytic reaction by the light irradiated from the light source part 120 and removes pollutants introduced into the HVAC case 300 and fungi, various pollutants, and an odor in the evaporator 410 by oxidation of the peroxygen radicals produced from the photocatalytic reaction.

More specifically, if the catalytic part 130 absorbs the light irradiated from the light source part 120, electrons of a valence band (VB) filled with electrons absorb the light energy to be jumped to a conduction band (CB) in which electrons are empty.

Holes which are in empty electron spots of the valence band oxidizes water molecules to be in their own original state and the oxidized water molecules form OH radicals.

In addition, electron called an excited electron excited to the conduction band reacts with oxygen to produce the peroxygen radicals having strong oxidizing power.

Meanwhile, as illustrated in FIG. 8, the catalytic part 130 of the photocatalytic apparatus 100 according to the exemplary embodiment of the present invention includes a cylindrical carrier 131 and a coating layer 132 fixed to the carrier 131 in which a catalyst liquefied in a gel state by adding a co-catalyst and an acidic additive is carried.

At this point, the catalytic part 130 is fixed to the body 110 so that a distance between the LED 121 of the light source part 120 and an end of a bottom surface of the carrier 131 is constant.

In other words, the carrier 131 has a cylindrical shape to have a circular bottom surface and is fixed so that a center of the bottom surface of the carrier 131 is opposite to the LED 121 to make an arrival distance of light irradiated from the LED 121 that is the light source constant, thereby considerably increasing the deodorizing and sterilizing power. In other words, in the catalytic part 130 of the photocatalytic apparatus 100 according to the exemplary embodiment of the present invention, the carrier 131 forming the catalytic part 130 has the cylindrical shape and the arrival distance of the light irradiated from one light source is constant, thereby considerably increasing the deodorizing and sterilizing power and reducing the manufacturing cost of the photocatalytic apparatus.

In addition, the carrier 131 which has a plurality of pores formed therein may be have various structures, including a mesh, and may be made of metal or materials having elasticity. The catalyst includes titanium oxide particulated at a size of 10 nm to 60 nm, and a surface area value of the titanium oxide may be 330 $m^2/g$ or more.

More specifically, the titanium oxide (TiO2) used as the photocatalyst receives ultraviolet rays of 400 nm or less to produce the peroxygen radicals, and the produced oxygen radicals decompose organic substances into safe water and carbon dioxide.

The titanium oxide is nano-particulated, and therefore may produce a large amount of peroxygen radicals even using a light source having a relatively weak ultraviolet wavelength. Therefore, the titanium oxide has excellent decomposing power of organic matters, has persistent durability and stability against the environmental change, and has a semi-permanent effect. In addition, the peroxygen radicals produced in large quantities may remove not only organic matters but also various substances such as odor and bacteria.

Since the catalytic part 130 forms the surface area of the nano-particulated titanium oxide into 330 $m^2/g$ or more, the number of particles that receive light energy per area is much larger than that of ordinary titanium oxide, such that the generation quantity of peroxygen radicals is increased.

At this point, the co-catalyst may be alumina. In this case, a carrying force of the catalytic part 130 may be further improved and the fixing ability of the carrier 131 may be increased.

Describing an example of a manufacturing process of the catalytic part 130, the titanium oxide suffers from a firing process at high temperature and a room-temperature drying process to be particulated at a size of 10 nm to 60 nm and then is processed in a liquid phase by being added with the co-catalyst made of alumina.

Thereafter, the liquid phase is secondarily processed to meet usage and is carried in the carrier 131, and suffers from a secondary drying and firing process to be fixed to the carrier 131.

As illustrated in FIGS. 5 and 6, the heat radiating parts 141 and 142 are provided in the light source part 120 to emit the heat generated from the light source part 120 and may include the first heat radiating fins 141.

It is very important to allow the first heat radiating fins 141 provided on the substrate 122 to radiate heat and the light source part 120 to emit the heat generated from the LED 121 and the substrate 122 so as to keep a light quantity high, such that the first heat radiating fins 141 are formed in an area other than an area where light is irradiated from the LED 121 to the catalytic part 130.

The first heat radiating fins 141 may be formed in various shapes, including a pin shape and a plate shape. When the first heat radiating fins 141 have the plate shape, the first heat radiating fins 141 may be formed on one side of the substrate 122 provided with the LED 121 in parallel in an air flow direction.

The area where light is irradiated from the LED 121 to the catalytic part 130 is present between the one side of the substrate 122 provided with the LED 121 inside the body 110 and the catalytic part 130 by the space forming part 113 of the body 110, and the first heat radiating fin 141 is provided to radiate heat through air flowing in the area.

As illustrated in FIG. 6, the first heat radiating fins 141 are formed in left and right directions of the drawing and may easily emit heat without blocking the light irradiated from the LED 121 by preventing the first heat radiating fins 141 from protruding in a central area in which the LED 121 is provided and by making the first heat radiating fins 141 be inclined downward in both directions of the drawing.

Further, unlike the light source part 120 including the LED 121 formed in one in the photocatalytic apparatus 100 according to the exemplary embodiment of the present invention, even when two or more LEDs 121 are provided, they may be freely formed in the area other than the area in which the light is irradiated to the catalytic part 130.

Further, as illustrated in FIG. 7, the heat radiating part may include the second heat radiating fins 142 provided on an opposite side of the substrate 122 on which the LED 121 is provided.

The second heat radiating fins 142 are formed on an opposite surface of the substrate 122 to the side where the first heat radiating fins 141 and the LEDs 121 are provided and may be formed on the substrate 122 or protrude from the support part 112 of the body 110 supporting the substrate 112 to emit the heat generated from the light source part 120.

In particular, when the second heat radiating fins 142 are formed on the substrate 122, the body 110 may be provided with a hollow part 112a in which a predetermined area of the support part 112 is hollow so that the second heat radiating fins 142 protrude toward the outside while being inserted into the body 110.

The photocatalytic apparatus 100 according to the exemplary embodiment of the present invention may include one or both of the first heat radiating fin 141 and the second heat radiating fin 142 to effectively emit the heat generated from the LED 121, thereby keeping the light quantity characteristics of the LED 121 high and increasing the durability to continuously maintain the sterilizing and deodorizing power.

The first heat radiating fins 141 and the second heat radiating fins 142 adhere to both surfaces of the substrate 122 and may be fastened at a time by a component for fixing the substrate 122 to the support part 112 of the body 110.

In addition, the substrate 122 of the photocatalytic apparatus 100 according to the exemplary embodiment of the present invention may be formed of a heat radiating substrate, and thus the substrate 122 itself may be the heat radiating part.

The photocatalytic apparatus 100 according to the exemplary embodiment of the present invention has a structure in which the peroxygen radicals are produced by the photocatalytic reaction using the light source part 120 and the catalytic part 130 and compared with the existing structure to adsorb and deodorize polluted air including an odor, may be used substantially semi-permanently by selecting a kind of carriers and appropriately controlling the light source part 120 to be turned on/off without separately replacing the filter.

Further, as illustrated in FIG. 9, in the photocatalytic apparatus 100 according to the exemplary embodiment of the present invention, the body 110 is preferably provided with a drainage hole 113a to discharge moisture therein.

At this point, the drainage hole 113a may be provided at a lower side of the space forming part 113 in the state in which it is mounted.

That is, the photocatalytic apparatus 100 according to the exemplary embodiment of the present invention is provided at a lower side of the inclined part 113 in the state where it is mounted on the HVAC case 300 of the HVAC equipment 1000 for a vehicle, such that moisture is guided to the drainage hole 113a through the inclined space forming part 113, thereby more increasing the water discharge effect.

In addition, the surface of the substrate 122 opposite to the catalytic part 130 is coated with a moisture-proof material, thereby preventing a malfunction and a failure due to moisture.

Meanwhile, as illustrated in FIGS. 10 to 12, the HVAC equipment 1000 for a vehicle of the present invention includes the HVAC case 300, the evaporator 410, the heater core 420, and the photocatalytic apparatus 100.

The HVAC case 300 is transferred with the introduced air, provided with a space in which the evaporator 410 and the heater core 420 are formed, and a vent 310 through which air is discharged.

In more detail, the HVAC case 300 is provided with the vent 310 through which air of which the temperature is controlled by the evaporator 410 and the heater core 420 is discharged to the interior of the vehicle.

The vent 310 includes a face vent 310, a defrost vent 310, and a floor vent 310.

The face vent 310 corresponds to a part discharging air toward a front side (front seat) of the interior of the vehicle, the defrost vent 310 corresponds to a part discharging air toward a window of the interior of the vehicle, and the floor vent 310 corresponds to a part discharging air toward a bottom of the front seat of the interior of the vehicle, and the face vent 310, the defrost vent 310, and the floor vent 310 have an opening value controlled by the respective mode doors 310d.

The side of the HVAC case 300 into which the air is introduced may be provided with a fan 214 for blowing air and an indoor air inlet 211 and an outdoor air inlet 212 are selectively open and closed by an indoor and outdoor air switching door 213 to transfer indoor air or outdoor air to the HVAC case 300 when the fan 214 is operated.

In more detail, the indoor air inlet 211 communicates with the inside of the vehicle to be introduced with indoor air and the outdoor air outlet 212 communicates with the outside of the vehicle to be introduced with an outdoor air.

The indoor and outdoor air switching door 213 is provided inside an inlet duct to open/close the indoor air inlet 211 and the outdoor air inlet 212. The indoor/outdoor air switching door 213 is operated in accordance with setting of vehicle passengers so as to control outdoor air or indoor air to be selectively introduced.

The evaporator 410 cools air using the flowing of a cold refrigerant and the heater core 420 heats air using the flowing of heated cooling water and the evaporator 410 and the heater core 420 are sequentially disposed in an air flow direction.

Further, the inside of the HVAC case 300 is provided with a temperature control door 320 for determining how much the air passing through the evaporator 410 passes through the heater core 420.

In other words, the temperature control door 320 controls an opening value of a hot air passage for completely passing the air, which passes through the evaporator 410, through the heater core 420 and a cold air passage for preventing the air passing through the evaporator 410 from passing through the heater core 420.

At this time, the photocatalytic apparatus 100 has features as described above, and is preferably provided at the front side of the evaporator 410 in the air flow direction to sterilize and deodorize the evaporator 410.

Further, the HVAC equipment 1000 for a vehicle according to the exemplary embodiment of the present invention has the advantage in that the photocatalytic apparatus 100 is mounted on one side of the HVAC case 300 to be easily mounted and detached, such that the photocatalytic apparatus may be easily checked and repaired and the hindrance of the air flow in the HVAC case 300 due to the photocatalytic apparatus 100 may be minimized.

In particular, in order to fix the photocatalytic apparatus 100 to the HVAC case 300, a predetermined area of the HVAC case 300 is hollow and thus a mounting hole 300a closed by the body 110 is formed, and the fixing part 111 is formed on the body 110.

FIG. 10 illustrates an example in which the HVAC case 300 is also hollow in a shape corresponding to the fixing part 111, has threads formed on an inner circumferential surface of the hollow area, and is fixed by a separate fastener 500, as an example in which the predetermined area of the fixing part 111 is hollow and threads are formed on an inner circumferential surface of the hollow area.

At this point, it is preferable that the fixing part 111 protrudes from the side where the support part 112 of the space forming part 113 is formed.

That is, the catalytic part 130 is located inside the HVAC case 300 and the space forming part 113 is located outside the HVAC case 300, with respect to the outer surface of the HVAC case 300.

Thereby, the HVAC equipment 1000 for a vehicle according to the exemplary embodiment of the present invention has the advantage in that the catalytic part 130 for purifying the air is positioned inside the HVAC case 300 to effectively purify air and the protruding degree into the HVAC case 300 is minimized to minimize the hindrance of the air flow.

Further, the space forming part 113 is positioned outside the HVAC case 300 with respect to the outer surface of the HVAC case 300, such that the moisture in the photocatalytic apparatus 100 may be easily discharged to the outside through the drainage hole 113a formed in the space forming part 113. (The left side of FIG. 10 is the outside of the HVAC case 300 and the right side thereof is the inside of the HVAC case 300).

The present invention is not limited to the above-mentioned exemplary embodiments, and may be variously applied, and may be variously modified without departing from the gist of the present invention claimed in the claims.

DETAILED DESCRIPTION OF MAIN ELEMENTS

100: Photocatalytic apparatus
110: Body
111: Fixing part
112: Support part
112a: Hollow part
113: Space forming part
113a: Drainage hole
114: Catalyst receiving part
114a: Stepped part
120: Light source part
121: LED
122: Substrate
130: Catalytic part
141: First heat radiating fin
142: Second heat radiating fin
131: Carrier
132: Coating layer
200: Blower
211: Indoor air inlet
212: Outdoor air inlet
213: Indoor and outdoor switching door
214: Blower fan
300: HVAC case
300a: Mounting hole
310: Vent
310d: Mode door
320: Temperature control door
410: Evaporator
420: Heater core
500: Fastener
1000: HVAC equipment for vehicle

The invention claimed is:

1. A photocatalytic apparatus, comprising:
a body;
a light source part including an LED and a substrate to which the LED is fixed to irradiate ultraviolet light and fixed to the body;
a catalytic part generating a photocatalytic reaction by light irradiated from the light source part while being fixed to the body to produce peroxygen radicals and including a cylindrical carrier and a coating layer fixed to the carrier in which a catalyst liquefied in a gel state by adding a co-catalyst and an acidic additive is carried; and
a heat radiating part provided in the light source part to emit heat generated from the light source part.

2. The photocatalytic apparatus of claim 1, wherein the catalytic part is fixed to the body so that a distance between the LED and an end of a bottom surface of the carrier is constant.

3. The photocatalytic apparatus of claim 1, wherein the body includes:
a support part supporting the substrate;
a space forming part extending from the support part and forming a gap between the LED and the catalytic part; and
a catalyst receiving part extending from the space forming part to fix the catalytic part.

4. The photocatalytic apparatus of claim 3, wherein the space forming part is inclined so that a width of the space forming part is widened in a light irradiating direction of the light source part from the support part.

5. The photocatalytic apparatus of claim 4, wherein the body is provided with a drainage hole through which moisture is discharged.

6. The photocatalytic apparatus of claim 5, wherein the drainage hole is formed at an inclined lower side of the space forming part in a state in which the photocatalytic apparatus is mounted.

7. The photocatalytic apparatus of claim 1, wherein a surface of the substrate opposite to the catalytic part is coated with a moisture-proof material.

8. The photocatalytic apparatus of claim 1, wherein the substrate is a heat radiating substrate.

9. The photocatalytic apparatus of claim 1, wherein the catalyst includes titanium oxide particulated at a size of 10 nm to 60 nm and a surface area value of the titanium oxide is 330 m$^2$/g or more.

10. The photocatalytic apparatus of claim 9, wherein the co-catalyst is alumina.

11. A heating, ventilating, and air conditioning (HVAC) equipment, comprising:
an HVAC case forming a space to which introduced air is transferred and provided with a vent through which air is discharged;
an evaporator provided inside the HVAC case;
a heater core provided at a back side of the HVAC case in an air flow direction; and
the photocatalytic apparatus of claim 1.

12. The HVAC equipment for a vehicle of claim 11, wherein the photocatalytic apparatus 100 is provided at a front side of the evaporator 410 in the air flow direction.

13. The HVAC equipment for a vehicle of claim 11, wherein a predetermined area of the HVAC case is hollow and thus a mounting hole closed by the body is provided, and the body is provided with a fixing part for being fixed to the HVAC case.

14. The HVAC equipment of claim 13, wherein in the photocatalytic apparatus, the fixing part protrudes from a side where the space forming part and the support part are formed so that the catalytic part is positioned inside the HVAC case and the space forming part is positioned outside the HVAC case, with respect to an outer surface of the HVAC case.

15. The HVAC equipment of claim 11, wherein the photocatalytic apparatus is mounted on one side of the HVAC case.

* * * * *